United States Patent [19]

Magistro

[11] 4,100,211

[45] Jul. 11, 1978

[54] PROCESS FOR PREPARATION OF ETHYLENE AND VINYL CHLORIDE FROM ETHANE

[75] Inventor: Angelo Joseph Magistro, Brecksville, Ohio

[73] Assignee: The BF Goodrich Company, Akron, Ohio

[21] Appl. No.: 686,908

[22] Filed: May 17, 1976

[51] Int. Cl.$^2$ ............................................. C07C 21/02
[52] U.S. Cl. ........................... 260/656 R; 260/683 R; 260/683.3; 252/411 R; 252/462; 252/466 J
[58] Field of Search ......... 260/683.3, 677 XA, 656 R; 252/411 R

[56] References Cited

U.S. PATENT DOCUMENTS

| | | | |
|---|---|---|---|
| 3,655,805 | 4/1972 | Croce et al. | 260/683.3 |
| 3,904,553 | 9/1975 | Campbell et al. | 252/466 J |
| 3,960,975 | 6/1976 | Manning | 260/683.3 |

Primary Examiner—Delbert E. Gantz
Assistant Examiner—Joseph A. Boska
Attorney, Agent, or Firm—Alan A. Csontos

[57] ABSTRACT

Ethylene and vinyl chloride are prepared in excellent yields by the reaction of ethane with a chlorine source in the presence of oxygen and a solid solution catalyst containing iron cations. The present invention comprises an improvement in the above process wherein the solid solution catalyst after exhibiting a loss in activity is regenerated in situ by the addition of an iron source such as $Fe(NO_3)_3$ to the ongoing process. After addition of the iron source, ethane conversion to products and yields of ethylene and vinyl chloride similar to that originally obtained using freshly prepared solid solution catalyst are achieved. Furthermore, the invention allows for extended operation of the process without loss of time and productivity due to possible interruptions caused by regeneration of the catalyst using known techniques.

7 Claims, No Drawings

4,100,211

PROCESS FOR PREPARATION OF ETHYLENE AND VINYL CHLORIDE FROM ETHANE

BACKGROUND OF THE INVENTION

Vinyl chloride ($CH_2=CHCl$) is prepared using a number of well known processes. Two familiar processes are (1) the hydrochlorination of acetylene and (2) the oxychlorination of ethylene to form dichloroethane which in turn is dehydrohalogenated to form vinyl chloride (see C. A. Schildknecht, *Vinyl and Related Polymers,* John Wiley and Sons, Inc., N.Y., N.Y. (1952), pages 388-390 and U.S. Pat. No. 2,847,483). As acetylene is more expensive than ethylene, the latter process is economically favored, and much activity is noted in this art area (see U.S. Pat. Nos. 3,634,330; 3,454,663; 3,448,057; and 3,624,170). Ethylene, in turn, can be prepared by the oxydehydrogenation of ethane (see U.S. Pat. No. 3,769,362). Although high yields of ethylene are particularly desired, processes which use ethane as a feed stock can produce not only ethylene, but also can directly produce vinyl chloride and other valuable products such as ethylene dichloride, ethyl chloride, and the like. The ethylene, ethylene dichloride, and ethyl chloride can be readily reacted to form more vinyl chloride.

The present invention is directed to an improved process for the preparation of ethylene and vinyl chloride from ethane which improvement comprises the in situ regeneration of a solid solution catalyst containing iron by the addition of an iron source to the ongoing process.

Catalysts containing iron are known in the art. See U.S. Pat. Nos. 3,907,713; 3,849,339; 3,769,362; 3,703,593; 3,658,934; 3,658,933; 3,207,811; 2,847,483; and 2,674,633, and British Patent No. 1,039,369. However, none of these patents disclose a solid solution catalyst. An article in the Journal of the American Ceramic Society, Vol. 43, No. 7 (1960), page 367, discloses ceramic compounds of lanthanum and iron. Two patents directed to the desirability of using specific supports for a catalyst are U.S. Pat. No. 3,454,663 (an $\alpha$-$Al_2O_3$ support) and U.S. Pat. No. 3,723,351 (a calcium sodium aluminum disilicate support). Recently issued U.S. Pat. No. 3,904,553 discloses the use of certain specific solid solutions as catalysts.

Known methods of catalyst regeneration include methods where the catalyst is physically removed from the reaction area and treated, often by heating or re-firing the catalyst in an oxidative atmosphere, and methods wherein the catalyst is treated in situ by varying the feed and/or reactant stream to the reactor area. Examples of these methods are disclosed in U.S. Pat. Nos. 3,551,506 and 3,870,764. U.S. Pat. No. 3,870,764 further discloses the post-addition of phosphorous to the reaction zone.

Other art considered in this application other than those patents and articles mentioned above is as follows: U.S. Pat. Nos. 3,173,962; 3,308,188; 3,308,193; 3,308,198; 3,429,901; 3,707,806; 3,707,809; 3,862,996; 3,904,552; 3,907,912; and 3,917,541, and British Patent No. 904,084.

SUMMARY OF THE INVENTION

The present invention comprises an improved process for the preparation of ethylene and vinyl chloride from ethane wherein a solid solution catalyst containing iron cations is regenerated in situ by the addition of an iron source such as, for example, $Fe(NO_3)_2$ to the ongoing process. The use of a solid solution catalyst in the process results in high yields of ethylene and high combined yields of ethylene and vinyl chloride. Employing the regeneration method of this invention results in an improved process because the solid solution catalysts can then exhibit their activity for hundreds of hours without need of interrupting the process for catalyst regeneration.

DETAILED DESCRIPTION OF THE INVENTION

Ethane is reacted with oxygen and a chlorine source and in the presence of a solid solution catalyst containing iron to prepare ethylene, vinyl chloride, and other valuable by-products. Depending upon feed and reactor conditions, about 30 to about 85 mole percent yield of ethylene and over a 90 mole percent total yield of ethylene and vinyl chloride can be obtained. Conversion of ethane to products can approach 100 mole percent.

In the process, ethane, oxygen and a chlorine source are placed into a reactor vessel containing a solid solution catalyst containing iron. The process can be operated as a batch process, but is preferably conducted at a continuous process wherein reactants and products are continuously added and withdrawn. The solid solution catalyst can be fixed in a bed, it can be supported, or it can be present as particles that can readily fluidize during operation. A preferred embodiment of the process is to employ the solid solution catalyst in particulate form that will fluidize in the process thereby establishing maximum contact with the reactants. Such processes are known as fluid bed processes, and the reactors designed for such are known as fluid bed reactors. A typical reactor is designed such that one or more gaseous reactants is introduced in the reactor below the catalyst bed, and the gas pressurized through the bed lifting and suspending the catalyst in the reactor volume. Other reactants can be added at appropriate levels above, below, or any point in the fluid catalyst bed. Normally, products are withdrawn from the top portion of the reactor and collected or further treated as desired.

The reactants comprise ethane, oxygen (usually used in the form of air), and a chlorine source. The chlorine source is preferably hydrogen chloride gas. Using one mole of ethane as a basis, the hydrogen chloride is used at from about 0.1 mole to about 10 moles or more. More preferably, the hydrogen chloride is used at a level of from about 0.5 mole to 5 moles per mole of ethane. In general, as a higher ratio of hydrogen chloride to ethane is used, the yield of vinyl chloride and other chlorinated products increases and the yield of ethylene decreases. However, levels of use of hydrogen chloride above 5 moles per mole of ethane also increase the amount of hydrogen chloride to recycle. Excellent results have been obtained using about 1 to about 4 moles of hydrogen chloride per mole of ethane. As both ethylene and vinyl chloride can be prepared in significant amounts using the catalysts and as the yield of ethylene to vinyl chloride is dependent upon the hydrogen chloride to ethane ratio in the reactant feed, the process can be termed either an oxydehydrochlorination process to prepare ethylene or an oxychlorination process to prepare vinyl chloride.

Oxygen, preferably in the form of dry air, is used at from about 0.1 mole to about 1.5 moles of oxygen to one mole of ethane. A more preferred level is from about 0.5 mole to about 1 mole. The use of levels of oxygen of about 1 mole per mole of ethane is preferred in an oxychlorination process. In an oxydehydrochlorination process, excellent results have been obtained using a level of oxygen of about 0.5 to 0.6 mole per mole of ethane.

Ethane, oxygen, and hydrogen chloride are put into the reactor as reactants. Temperature of the reaction ranges from about 400° C. to about 650° C., and more preferably from about 475° C. to about 600° C. Materials withdrawn from the reactor in the product stream comprise ethylene, vinyl chloride, chlorinated products such as ethylene dichloride and ethyl chloride, carbon oxides (CO and $CO_2$), water, and unreacted ethane and hydrogen chloride.

An important feature of the process is the use as a catalyst of a solid solution catalyst containing iron cations substituted for cations in the host lattice. The catalyst is basically a solid solution of iron cations in a host lattice. This is in contrast to catalysts wherein an active ingredient such as cupric chloride or iron oxide is merely absorbed onto the surface of a support structure or material. The difference can be distinguished both in the physical state of the catalyst and in the activity of the catalyst.

The solid solution catalyst is a true solution wherein iron cations are substituted for host lattice ions in the catalyst structure. An X-ray diffraction pattern of a solid solution catalyst is characteristic of the diffraction pattern of the host lattice. For example, a solid solution catalyst of $Fe_2O_3$ in $\alpha$-$Al_2O_3$ will exhibit an X-ray diffraction pattern characteristic of $\alpha$-$Al_2O_3$. In contrast, if $Fe_2O_3$ is merely absorbed onto $\alpha$-$Al_2O_3$, the X-ray diffraction pattern will show the presence of both $Fe_2O_3$ and $\alpha$-$Al_2O_3$.

A distinguishing feature of the solid solution catalysts is in the increased selectivity and retention of iron by the catalyst upon use. For example, a solid solution catalyst of iron cations in $\alpha$-$Al_2O_3$, used at reaction conditions of 1 mole ethane/1 mole oxygen/4 moles hydrogen chloride, lost about 15% by weight of its original iron content after 100 hours of use. In contrast, a catalyst comprised of ferric oxide merely absorbed onto $Al_2O_3$, operating under the same set of conditions, lost about 85% by weight of its original iron content after 100 hours of use.

Solid solution catalysts containing iron cations can be of different types. The iron exists as ferric ($Fe^{+3}$) and/or ferrous ($Fe^{+2}$) ions. The ferric ion is the active ion in the catalyst. However, as the ferrous ion can oxidize to a ferric ion in the process, the use of solid solution catalysts containing ferrous ions is within the scope of the invention.

In the solid solution catalyst containing iron cations, there is direct substitution of iron ions for host lattice ions. An example of this catalyst is $(Fe_x^{+3}M_{2-x}^{+3})O_3$ wherein x is greater than 0 and less than 2 and M is a metal such as Al or Cr. An example of this is a solid solution catalyst of ferric oxide ($Fe_2O_3$) in aluminum oxide ($Al_2O_3$). As the ferric ion is much greater in size than an aluminum +3 ion, the solubility of the ferric ion in aluminum oxide is limited. Hence, the solid solution catalysts of the example wherein M is aluminum encompass materials of the formula wherein x has an upper limit of about 0.15.

The solid solution catalyst containing iron can be further stabilized against iron loss by using lanthanum and/or a lanthanide. Although the lanthanum or lanthanide, if used, is an integral part of the catalyst, it is believed that the lanthanum or lanthanide does not enter into solid solution with the host lattice as does the iron. Characterization of the catalysts will be discussed further in a subsequent section of the application.

The lanthanum and lanthanides can be employed in the solid solution catalysts singly or as mixtures of the metals. The lanthanides are elements 58 to 71 of the Periodic Table. More preferably, the lanthanides used are cerium, praeseodymium, neodymium, and erbium. Excellent results have been obtained in the process using a catalyst of $Fe_2O_3$ in $\alpha$-$Al_2O_3$ stabilized with lanthanum.

The solid solution catalyst containing iron and stabilized with lanthanum or a lanthanide can be further modified with select metal cations. The use of these cations results in a catalyst having even further improved selectivity for the formation of vinyl chloride and/or increased catalyst lifetime. The metal cations employed are selected from the group consisting of lithium, magnesium, chromium, manganese, cobalt, and copper. Excellent results have been obtained using cobalt to modify the catalyst to achieve significant increases in catalyst lifetime, and manganese to modify the catalyst to achieve more selectivity for vinyl chloride.

Although the selected metal cation, if used, is an integral part of the catalyst, it is believed that the selected metal does not enter into solid solution with the host lattice as does the iron.

SOLID SOLUTION CATALYST IDENTIFICATION AND CHARACTERIZATION

The solid solution catalysts used in the invention contain iron and have X-ray diffraction patterns characteristic of the host lattice material. Solid solutions are known to exist (see C. S. Barrett, *Structure of Metals, Crystallographic Methods, Principles, and Data*, 2nd Ed., McGraw-Hill Book Co., Inc., N.Y., N.Y. (1952) at pages 220 et seq. and U.S. Pat. No. 3,904,553).

The catalyst is first identified and characterized by analyzing it to determine what elements it contains. This can be done using well known techniques such as chemical analysis, atomic absorption spectroscope, X-ray fluorescence spectroscopy, and optical microscopy. For example, the solid solution catalyst of iron oxide in aluminum oxide, stabilized with lanthanum and modified with cobalt, would show iron, lanthanum, aluminum cobalt, and oxygen to be present in the catalyst. The presence and quantity of iron in the catalyst can be readily determined using a standard method of chemical analysis such as the dichromate method for the determination of iron. The amount of iron in the solid solution catalysts is limited by the solubility of the ions in the host lattice. The solid solution catalysts of the invention contain from about 0.1 percent to 20 percent by weight and more preferably from about 0.5 percent to about 10 percent by weight of iron in the catalyst, the weight percent expressed as the oxide. The catalyst can further contain lanthanum and/or lanthanide in up to 20 percent and preferably from about 0.5 percent to 10 percent by weight, the weight percent expressed as the oxide. The selected metal cation can be present in the solid solution catalyst in up to about 3 percent by weight and more preferably in from about 0.1 percent to about 0.5 percent by weight of the catalyst, the weight percent expressed as the oxide of the selected metal.

The second step of identification and characterization involves running an X-ray diffraction scan on the catalyst. The X-ray diffraction scan will show a pattern of peaks, which peaks have positions and intensities distinctive of the crystalline phases which are present. The X-ray diffraction peak positions and intensities of the catalyst can be compared to peak positions and intensities of known crystalline phases that are published (in the ASTM Powder Diffraction File, for example), or that are experimentally obtained. For example, a catalyst comprised of iron oxide merely impregnated on aluminum oxide will have an X-ray diffraction pattern of peak positions showing the distinct peak positions and intensities of iron oxide and aluminum oxide crystalline phases.

In contrast, the X-ray diffraction pattern of a solid solution catalyst containing iron shows the positions of the X-ray diffraction peaks in the solid solution catalyst to be shifted from the peak positions in the X-ray diffraction pattern of the host lattice. The shift in peak positions may be accompanied by changes in the relative intensities of the peaks, but the intensity changes are generally small.

The shift in X-ray diffraction peak positions when solid solutions are formed results from the expansion (or contraction) of the dimensions of the unit cell of the crystalline phase of the host lattice. The dimensions of the unit cell of the host lattice are changed due to the substitution of iron cations for cations of the host lattice. If the cation is larger than the cation it displaces, the unit cell dimensions will increase in size to accommodate the larger cation. The amount of expansion (or contraction if the iron cation is smaller than the host lattice cation it displaces) of the unit cell dimensions can be determined by calculating the lattice parameters of the unit cell of the solid solution phase and comparing these lattice parameters to the lattice parameters of the unit cell of the host. A change in lattice parameters due to iron substitution in a crystalline host lattice is frequently in accordance with Vegard's law (see page 221 of the above-cited reference). Since a change in the lattice parameters causes a change in the X-ray diffraction peak positions, a quick comparison of the X-ray diffraction pattern of the catalyst and the pattern of the host lattice will show whether a solid solution catalyst has been prepared.

Alternately, a more accurate method of confirming the preparation of a solid solution catalyst is to experimentally run X-ray diffraction scans of the prepared catalyst and of the host lattice and then calculate the lattice parameters of each. If the values obtained for the lattice parameters of the catalyst and host lattice are different, a solid solution catalyst has been prepared. If the geometry and dimensions (lattice parameters) of the unit cell of the host lattice is not known, it can be determined using established methods for indexing and interpreting X-ray diffraction patterns (see L. V. Azaroff and M. J. Buerger, *The Powder Method in X-ray Crystallography*, McGraw Book Co., Inc., N.Y., N.Y. (1958), chapters 6 to 13). The high $2\theta$ values (where $\theta$ is the Bragg angle) are normally used to calculate the lattice parameters.

In the case of a solid solution catalyst stabilized with lanthanum and/or a lanthanide and modified with a selected metal, the X-ray diffraction pattern will clearly show the presence of the solid solution, which is the primary crystalline phase, and will additionally show the presence of crystalline lanthanum and/or lanthanide and selected metal compounds which are present in detectable amounts. For example, in the case of a solid solution catalyst of $Fe_2O_3$ in $\alpha\text{-}Al_2O_3$ stabilized with lanthanum and modified with cobalt, the X-ray diffraction pattern will show the presence of the $Fe_2O_3$ in $\alpha\text{-}Al_2O_3$ solid solution crystalline phase, the crystalline compounds of lanthanum such as $La_2O_3$ and $LaAlO_3$, and crystalline cobalt oxide.

In summary, the solid solution catalysts used in the invention can be identified and characterized by (1) the presence of iron, and of lanthanum and/or lanthanides, if used, and the selected metal, if used, in the catalyst, and (2) the X-ray diffraction pattern of the catalyst. The iron is present as cations substituted in the host lattice for cations of the host lattice. The iron content can be measured using standard analysis techniques. The X-ray diffraction pattern of the solid solution catalyst will exhibit peak positions characteristic of the host lattice but shifted due to the presence of the iron cations in the host lattice. Lattice parameters calculated for the host lattice and the solid solution catalyst will differ. The X-ray diffraction pattern of the solid solution catalysts of the invention will exhibit extraneous peaks in the pattern due to formation of crystalline compounds other than the solid solution catalyst itself, such as lanthanum oxide or lanthanide oxides, and selected metal oxides.

PREPARATION OF SOLID SOLUTION CATALYSTS OF THE EXAMPLES

The solid solution catalysts used in the Examples were prepared by first impregnating a host lattice precursor with an iron salt and, if desired, a lanthanum salt and a selected metal salt or precursor that yields the oxides upon heating, then heating the impregnated host lattice precursor to about 550° C. followed by heating to 1200° C. or more. The first heat treatment converts the salts to oxides, and initiates conversion of the host lattice precursor to the host lattice. The second heat treatment completes the formation of the host lattice and produces a rearrangement of the metal atoms between the metal ions in the host lattice and the iron ions. The catalyst prepared is a solid solution catalyst containing iron which can be stabilized with lanthanum and/or lanthanides and modified with the selected metal. The catalyst has a distinctive X-ray diffraction pattern.

The solid solution catalyst can be prepared in other different ways. Another method is to physically admix iron oxide, lanthanum or a lanthanide oxide (if used), the selected metal oxide (if used), and the host lattice material and heat the mix to allow dissolution and substitution of the iron ions for those of the host lattice, and formation of the stabilized and modified catalyst. Heating conditions vary for the nature of the host lattice employed, but typically are above 1100° C.

A third method of preparation is to use the socalled sol-gel process wherein an iron salt, lanthanum and/or lanthanide salt (if used), selected metal salt (if used), and a salt precursor of the host lattice are mixed together as solutions and a base is added to co-precipitate out a mixture of the corresponding hydrated oxides. For example, ferric nitrate, lanthanum nitrate, cobalt nitrate, and aluminum nitrate can be dissolved in water and ammonium hydroxide added to the solution to co-precipitate a mixture of hydrated iron, lanthanum, cobalt, and aluminum oxides. The mix is then heated to above 1100° C. to perfect dissolution and substitution of the iron ions for aluminum ions.

A fourth method is to dissolve a lanthanum or lanthanide salt and a selected metal salt in a solvent such as water or ethanol and use the solution to impregnate a preformed solid solution catalyst containing iron, and then dry and heat the mix to cause the metal salt to decompose upon heating to yield the oxide(s).

In all of these methods a metal oxide precursor can be used in place of the metal oxide per se. The precursor, which is typically a salt of the metal, decomposes on heating to yield the oxide form of the metal. Examples of iron oxide precursors are iron chloride, iron sulfate, iron formate, iron oxalate, iron citrate, iron nitrate, and the like. Precursors of the oxides of lanthanum or lanthanides and of the selected metals can also be employed. Examples of lanthanum oxide precursors are lanthanum nitrate, lanthanum chloride, lanthanum sulfate, lanthanum oxalate, and the like. Examples of selected metal oxide precursors are lithium nitrate, lithium oxalate, magnesium nitrate, magnesium chloride, chromium acetylacetonate, chromium chloride, manganese chloride, manganese oxalate, manganese nitrate, cobalt chloride, cobalt nitrate, and cobalt oxalate.

The solid solution catalysts can be used in the process in the form of a fixed bed, a fluidized bed, on a fixed support, on a fluidized support, or in a number of ways well known to the art. Although in the examples the process used is a fluidized bed process, it is understood that other known processes can be employed.

IN SITU REGENERATION OF SOLID SOLUTION CATALYST

As previously mentioned, the rate of iron loss of a solid solution catalyst is significantly less than that of an impregnated catalyst. This substantial improvement in iron retention can be further dramatically improved by the use of lanthanum or lanthanides and select metal cations in the solid solution catalyst. However, iron loss does occur, and with it is seen a decrease in catalyst activity, i.e., a decrease in percent conversion of ethane to products and a decrease in mole percent yield of ethylene and vinyl chloride. It has been unexpectedly discovered that the solid solution catalysts, after exhibiting a loss in activity in the process, can be regenerated in situ by the addition of an iron source to the ongoing process. Upon addition of the iron source, catalyst activity is comparable to the activity originally exhibited and this activity remains for a period similar to that originally observed. As the original activity of the catalyst can be very high for 200 hours or more, and this activity can be regained and retained by the addition of iron, the process of the invention allows for hundreds of hours of continuous operation without the need to use disruptive catalyst regeneration techniques taught in the art.

The iron source is added directly to the ongoing process preferably at a point close to the catalyst bed. Process temperatures and pressures and reactant ratios do not have to be adjusted. Regeneration of the solid solution catalyst occurs in a matter of a few hours. The conversion of ethane to products and the yield of ethylene and vinyl chloride obtained after addition of the iron source is similar to that originally observed using freshly prepared solid solution catalyst. It is believed that the iron introduced into the process at the reaction conditions is taken into the catalyst at the sites where the iron is lost to reform the solid solution structure.

The iron source can be iron oxide or an iron precursor such as those previously mentioned in the section dealing with the formation of the solid solution catalysts. Examples of iron precursors are iron chloride, iron sulfate, iron formate, iron oxalate, iron citrate, iron nitrate, iron acetate, iron acetylacetate, and the like. Excellent results have been obtained using $Fe(NO_3)_3$ as the iron source in the regeneration of the catalyst.

The following examples are given to further illustrate the process of the invention.

EXAMPLES

Solid solution catalysts were used in processes to react ethane to ethylene and to vinyl chloride. The reactions were conducted in a fluid bed reactor wherein the ethane, oxygen (used in the form of air), and chlorine source (anhydrous HCl) were premixed at a set molar ratio of reactants and the mixture fed into a heated reactor near the bottom. The catalyst used was in the form of particles of a size passing between 80 mesh and 325 mesh screens. Contact times in the reaction were from about 4 seconds to about 8 seconds. Products were withdrawn from the top of the reactor as gases, scrubbed with water and analyzed using a gas chromatograph. The process was run as a continuous process for times up to 550 hours per run.

The following examples detail experiments conducted using various mole ratios of reactants, various temperatures and times of reaction, and different solid solution catalysts.

COMPARATIVE EXAMPLES

Experiments were conducted to compare ethane conversion, yield of ethylene and vinyl chloride obtained, and retention of iron on use between (a) solid solution catalysts and (b) an iron-impregnated catalyst.

Experiment A

The catalysts employed in the process were prepared by the following procedures.

A solution of 16.0 grams of $La(NO_3)_3 \cdot 6H_2O$, 0.75 grams of $Co(NO_3)_2 \cdot 6H_2O$, and 14.9 grams of $Fe(NO_3)_3 \cdot 9H_2O$ dissolved in about 125 milliliters of ethanol was added to 141.1 grams of $Al_2O_3 \cdot 3H_2O$ (sold by Alcoa Co. as C-31) and the ethanol evaporated off. The mixture was then heated at 560° C. for 16 hours to dehydrate the alumina trihydrate and to decompose the ferric nitrate, cobalt nitrate, and lanthanum nitrate to ferric oxide, cobalt oxide, and lanthanum oxide. The catalyst was then further heated at 1200° C. for 16 hours to cause formation of the solid solution catalyst. The catalyst is a solid solution of 2% by weight of $Fe_2O_3$ in $\alpha$-$Al_2O_3$ stabilized with 4% by weight of $La_2O_3$ and modified with 0.2% by weight of CoO.

The unmodified but lanthanum stabilized solid solution catalyst of iron oxide in $\alpha$-aluminum oxide was prepared in the same manner as recited above but without any cobalt oxide precursor present. Hence, this solid solution catalyst is not modified with cobalt. The catalyst is a solid solution catalyst of 2% by weight of $Fe_2O_3$ in $\alpha$-$Al_2O_3$ stabilized with 4% by weight of $La_2O_3$.

The impregnated catalyst employed in this example was prepared by impregnating aluminum oxide with a solution of ferric nitrate, drying the mix, and then heating the mix for 16 hours at 550° C. The preparation is similar to the preparation of the solid solution catalysts except that no heat treatment at 1200° C. was done.

X-ray diffraction analysis of the impregnated catalyst showed two distinct phases, i.e., the impregnated catalyst was a mixture of $Fe_2O_3$ and $Al_2O_3$. The catalyst is an impregnated catalyst of 2% by weight of $Fe_2O_3$ on $\alpha$-$Al_2O_3$.

The catalysts were individually placed into a reactor and the reactants fed into the reactor at a mix of 1 mole ethane/0.6 mole of oxygen (as air)/1.5 moles of anhydrous hydrogen chloride. The reaction was run as an oxydehydrochlorination reaction process to obtain high yields of ethylene. Contact time throughout the runs was about 5 seconds. Temperature of reaction was about 550° C. Results are given in the following tables.

| | Modified and Stabilized Solid Solution Catalyst | | |
|---|---|---|---|
| | Mole % | % Yield of | |
| Time (Hrs.) | Conversion of Ethane | Ethylene | Vinyl Chloride |
| 2 | 82.0 | 81.6 | 6.9 |
| 20 | 83.2 | 80.9 | 6.2 |
| 44.5 | 84.6 | 80.5 | 6.2 |
| 72 | 80.2 | 80.6 | 5.9 |
| 96 | 86.1 | 79.0 | 6.6 |
| 119 | 77.3 | 79.5 | 6.3 |
| 148 | 82.3 | 79.7 | 6.1 |

| | Unmodified But Stabilized Solid Solution Catalyst | | |
|---|---|---|---|
| | Mole % | % Yield of | |
| Time (Hrs.) | Conversion of Ethane | Ethylene | Vinyl Chloride |
| 1.5 | 89.7 | 75.4 | 14.7 |
| 5 | 86.9 | 78.8 | 12.7 |
| 27 | 88.6 | 80.9 | 9.7 |
| 48 | 86.8 | 81.4 | 9.3 |
| 71 | 86.0 | 81.0 | 7.6 |
| 96.5 | 82.3 | 81.9 | 6.0 |
| 105 | 86.5 | 82.4 | 7.5 |
| 125 | 85.2 | 80.6 | 6.6 |

The data shows that the use of solid solution catalysts results in significantly higher mole percent conversion of ethane to products and higher yield of ethylene and vinyl chloride than the use of the impregnated catalyst. The stabilized and modified solid solution catalyst lost only 0.2% of its original iron content after 165 hours of use. The stabilized but unmodified solid solution catalyst used above lost 3.1% of its original iron content after 97 hours and 4.7% of its original iron content after 203 hours of use. The simple catalyst of iron oxide impregnated on aluminum oxide lost 8.4% of its original iron content after 90 hours of use.

Experiment B

Experiments were conducted to compare ethane conversion, yield of vinyl chloride, and iron loss between a solid solution catalyst of this invention and an iron-impregnated catalyst. The solid solution catalyst used was a solid solution of 4% by weight of $Fe_2O_3$ in $\alpha$-$Al_2O_3$ (prepared following the procedure given above). The impregnated catalyst employed was prepared by impregnating $\alpha$-aluminum oxide with a solution of ferric nitrate, drying the mix, and then heating the mix for 16 hours at 550° C. to dehydrate the aluminatrihydrate and to decompose the ferric nitrate to ferric oxide. The preparation is the same as used to prepare the solid solution catalyst except that no heat treatment at 1200° C. was done. X-ray diffraction analysis of the impregnated catalyst showed two distinct phases, i.e., the impregnated catalyst was a mixture of $Fe_2O_3$ and $\alpha$-$Al_2O_3$. The reactants were fed into the reactor at a mix of 1 mole ethane/1 mole of oxygen (as air)/4 moles of anhydrous hydrogen chloride. Contact time throughout the runs ranged from 5.7 to 7.8 seconds. Temperature of reaction was 550° C. Results are given in the following tables.

| | Solid Solution Catalyst | |
|---|---|---|
| Time (Hrs.) | Mole % Conversion Of Ethane | % Yield of Vinyl Chloride |
| 2 | 97.8 | 32.1 |
| 5 | 98.2 | 33.4 |
| 26 | 97.8 | 34.1 |
| 48 | 98.2 | 33.6 |
| 84 | 97.9 | 34.5 |
| 102 | 91.8 | 24.2 |
| 107 | 93.6 | 23.1 |

| | Impregnated Catalyst | |
|---|---|---|
| Time (Hrs.) | Mole % Conversion Of Ethane | % Yield of Vinyl Chloride |
| 1 | 99.0 | 23.8 |
| 5 | 98.2 | 26.8 |
| 31 | 99.2 | 26.9 |
| 55 | 99.2 | 28.6 |
| 62 | 98.4 | 31.0 |
| 99 | 97.4 | 29.6 |
| 109 | 99.0 | 27.7 |
| 119 | 98.8 | 24.2 |
| 141 | 97.6 | 17.5 |

The data show that the solid solution catalyst of the invention and the impregnated catalyst are somewhat comparable in mole % conversion of ethane. However, the greater activity of the solid solution catalyst is demonstrated by the significantly higher yields of vinyl chloride.

Another major difference between the two catalysts appears in the iron loss sustained by each catalyst. Results are reported in the following table. Iron content was determined using the dichromate process for the determination of iron.

| Time | Percent Iron Retained | |
|---|---|---|
| (Hrs.) | Solid Solution | Impregnated |
| 0 | 100 | 100 |
| 26 | 97.1 | — |
| 28 | — | 67.1 |
| 48 | 94.9 | — |
| 51 | — | 43.6 |
| 83 | 86.9 | — |
| 101 | — | 15.0 |
| 107 | 85.4 | — |

The data show that after about 100 hours of reaction time, the solid solution catalyst lost only about 15% by weight of its initial iron content, while the impregnated catalyst lost about 85% by weight of its iron.

Experiment C

The solid solution catalysts can be regenerated when they show a loss in activity to give conversions and yields comparable to original values. The conversion and yield data in the preceding tables show that at about 15% loss of iron in the solid solution catalyst (at about 100 hours), the activity of the catalyst decreased. The following experiment shows one method of regenerating the solid solution catalyst. The solid solution catalyst of 4% by weight $Fe_2O_3$ in $\alpha$-$Al_2O_3$ was physically removed from the reactor area and first heated to 550° C. for 2 hours in pure oxygen and then evaluated for its activity. No increase in activity was observed. This demonstrates that the regeneration of solid solution catalysts is not simply a reoxidation process. The solid solution catalyst was again physically removed from the reactor area and then heated to 1300° C. for 20 hours and again evaluated for its activity. The catalyst activity was excellent and comparable to its original activity. Data is given in the following table.

| | Solid Solution Catalyst | |
|---|---|---|
| | Mole % Conversion of Ethane | % Yield of Vinyl Chloride |
| Original Catalyst | | |
| at 2 hours | 97.8 | 32.1 |
| at 5 hours | 98.2 | 33.4 |
| at 107 hours | 93.6 | 23.1 |
| Oxidation Treated | | |
| at 1.25 hours | 90.9 | 21.9 |
| Heat Treated | | |
| at 5 hours | 98.4 | 34.0 |

Experiment C shows one method of regenerating a solid solution catalyst. However, this method is disruptive of the process in view of the fact that the catalyst has to be physically removed from the reaction area and treated. The method of regeneration of the catalyst in the present invention, as described in the following examples, is much preferred.

EXAMPLE I

The previous comparative examples showed that the solid solution catalysts lose iron at a much lower rate than does a mere iron-impregnated catalyst. However, the data in the comparative examples also shows that some iron loss does occur with a resultant decrease in activity of the catalyst, particularly in the yield of vinyl chloride. The solid solution catalysts can be regenerated in situ by the addition of an iron source to the ongoing process. The following data demonstrates this fact.

The solid solution catalyst employed is a catalyst of 2% by weight of iron, expressed as the iron oxide, in $\alpha$-$Al_2O_3$ stabilized with 4% by weight of lanthanum, expressed as lanthanum oxide. The catalyst is the same as that prepared in the Comparative Example in Experiment A. The process used was a fluid bed reaction process wherein the solid solution catalyst in particulate form was suspended in the reaction area by the flow of reactants. The feed stream to the reactor was 1 mole of ethane, 1.5 moles of hydrogen chloride, and 0.6 mole of oxygen (in the form of air). Temperature of reaction was 550° C. and contact time in the reactor area was about 5 seconds. The following results were obtained.

| Time (Hrs.) | % Conversion Of Ethane | Mole % Yield Of Ethylene | Mole % Yield Of Vinyl Chloride | Combined Yield |
|---|---|---|---|---|
| 1.5 | 89.7 | 75.5 | 14.7 | 90.2 |
| 5 | 86.9 | 78.7 | 12.7 | 91.4 |
| 27.5 | 88.6 | 80.9 | 9.7 | 90.6 |
| 48 | 86.8 | 81.4 | 9.3 | 90.7 |
| 71 | 86.0 | 81.0 | 7.6 | 88.6 |
| 96.5 | 82.3 | 81.9 | 6.0 | 87.9 |
| 105 | 86.5 | 82.4 | 7.5 | 89.9 |
| 125 | 85.2 | 80.6 | 6.6 | 87.2 |
| 173 | 77.0 | 80.5 | 3.7 | 84.2 |
| 178 | 83.1 | 79.3 | 4.7 | 84.0 |
| 203 | 72.0 | 77.9 | 2.7 | 80.6 |
| $Fe(NO_3)_3$ at 43% by weight of the original weight of iron was added to the reactor area immediately above the fluidized catalyst bed near the product exit port. | | | | |
| 205 | 89.7 | 82.1 | 12.0 | 94.1 |
| 227 | 95.1 | 79.8 | 11.8 | 91.6 |
| 249 | 92.1 | 82.1 | 9.7 | 91.8 |
| 279 | 93.3 | 82.8 | 8.5 | 91.3 |
| 302 | 90.8 | 84.4 | 7.3 | 91.7 |
| 329 | 89.7 | 83.0 | 8.7 | 91.7 |
| 350.5 | 90.9 | 81.4 | 9.8 | 91.2 |
| 359 | 90.6 | 83.4 | 8.9 | 92.3 |
| 382.5 | 90.8 | 83.4 | 8.5 | 92.9 |
| 403.5 | 91.8 | 83.5 | 7.7 | 91.2 |
| 432 | 90.8 | 84.1 | 8.2 | 92.3 |
| 451 | 91.2 | 83.9 | 8.9 | 92.8 |
| 498 | 92.9 | 85.2 | 7.9 | 93.1 |
| 522 | 91.7 | 83.5 | 8.8 | 92.3 |
| 546.5 | 91.7 | 85.1 | 7.7 | 92.8 |

As can be seen in the data, the original activity of the solid solution catalyst was quite high. However, after 200 hours of operation this activity had decreased substantially, particularly as evidenced by the decrease in percent conversion of ethane and the mole % yield of vinyl chloride. After addition of the iron source, $Fe(NO_3)_3$, to the ongoing reaction, the activity of the catalyst dramatically increased, particularly as evidenced by the increase in percent conversion of ethane and mole % yield of vinyl chloride.

EXAMPLE II

The experiment in Example I was essentially repeated using a solid solution catalyst of 2% by weight of iron, expressed as the oxide, in $\alpha$-$Al_2O_3$ stabilized with 4% by weight of lanthanum and modified with 0.2% by weight of cobalt, both weight percents expressed as the oxide. The catalyst is the same as that prepared in the Comparative Example in Experiment A. Results are seen in the following table.

| Time (Hrs.) | % Conversion Of Ethane | Mole % Yield Of Ethylene | Mole % Yield Of Vinyl Chloride | Combined Yield |
|---|---|---|---|---|
| 2 | 82.0 | 81.6 | 6.9 | 88.5 |
| 20 | 83.2 | 80.9 | 6.2 | 87.1 |
| 44.5 | 84.6 | 80.5 | 6.2 | 86.7 |
| 72 | 80.2 | 80.6 | 5.9 | 86.5 |
| 96 | 86.1 | 79.0 | 6.6 | 85.6 |
| 119 | 77.3 | 79.5 | 6.3 | 85.8 |
| 148 | 82.3 | 79.7 | 6.1 | 85.8 |
| 175.5 | 87.4 | 81.1 | 7.3 | 88.4 |
| 199.5 | 82.3 | 80.9 | 6.4 | 87.3 |
| $Fe_2O_3$ at 6 percent by weight of the original weight of iron was added to the reactor area immediately above the fluidized catalyst bed near the product exit port. | | | | |
| 218 | 87.2 | 84.1 | 8.1 | 92.2 |
| 234.5 | 93.8 | 82.2 | 10.9 | 93.1 |
| 253.5 | 89.1 | 83.8 | 9.1 | 92.9 |

Again the activity of the solid solution catalyst increased upon addition of the iron source, $Fe_2O_3$, to the ongoing process. The lanthanum stabilized and cobalt modified solid solution catalyst retains the iron more tenaciously than the solid solution catalyst which is only lanthanum stabilized (as can be seen in the data in the Comparative Examples, Experiment A). Hence, less iron loss occurred after 200 hours of use, and the effect of catalyst regeneration was less dramatic than in Example I.

I claim:

1. A process for the reaction of ethane to ethylene and vinyl chloride comprising (1) contacting ethane, oxygen, and a chlorine source in the presence of a solid solution catalyst of iron cations substituted for aluminum cations in a host lattice of $\alpha$-$Al_2O_3$ at a temperature from about 400° C. to about 650° C. wherein the ethane, oxygen, and chlorine source are employed at a molar ratio of 1 mole of ethane to 0.1 to 10 moles of the chlorine source to 0.1 to 1.5 moles of oxygen, said solid solution catalyst having an iron content of from about 0.1 percent to 20 percent by weight expressed as the oxide, (2) adding an iron source to the ongoing process to regenerate the solid solution catalyst in situ, and (3)

removing the products produced from the reaction area.

2. A process of claim 1 where in (1) the solid solution catalyst employed is a catalyst of from about 0.5 percent to about 10 percent by weight of iron, expressed as the oxide, substituted for aluminum cations in an alpha aluminum oxide wherein iron cations are substituted for aluminum cations in the host lattice, which catalyst is stabilized with up to 20 percent by weight expressed as the oxide, of lanthanum, a lanthanide, or mixtures thereof and modified with up to 3 percent by weight of a metal cation(s) selected from the group consisting of lithium, magnesium, chromium, cobalt, manganese, and copper, the weight percent expressed as the oxide, and in (2) the iron source is selected from the group consisting of iron chlorate, iron sulfate, iron formate, iron citrate, iron acetate, iron acetylacetate, iron nitrate, and iron oxide.

3. A process of claim 2 where in (1) the chlorine source is hydrogen chloride and the molar ratio employed is 1 mole of ethane to 0.5 to 1 mole of oxygen to 0.5 to 5 moles of hydrogen chloride, and the temperature of reaction is from about 475° C. to about 600° C.

4. A process of claim 3 where in (1) the solid solution catalyst contains iron cations substituted for aluminum cations in an $\alpha$-$Al_2O_3$ host lattice and is stabilized with from about 0.5 percent to about 10 percent by weight of lanthanum, expressed as the oxide, and in (2) the iron source is iron nitrate or iron oxide.

5. A process of claim 4 where in (1) the solid solution catalyst contains iron cations substituted for aluminum cations in an $\alpha$-$Al_2O_3$ host lattice and is stabilized with from about 0.5 percent to about 10 percent by weight of lanthanum and modified with from about 0.1 percent to about 0.5 percent by weight of cobalt cations or manganese cations, both weight percents expressed as the oxide, and in (2) the iron source is iron nitrate or iron oxide.

6. A process of claim 5 wherein the solid solution catalyst employed is a catalyst of iron cations substituted for aluminum cations in an $\alpha$-$Al_2O_3$ host lattice stabilized with lanthanum and modified with cobalt cations, and the iron source is iron oxide.

7. A process of claim 5 wherein the solid solution catalyst employed is a catalyst of iron cations substituted for aluminum cations in an $\alpha$-$Al_2O_3$ host lattice stabilized with lanthanum, and the iron source is iron nitrate.

* * * * *